United States Patent [19]

Sharkey

[11] Patent Number: 4,628,117
[45] Date of Patent: Dec. 9, 1986

[54] PROCESS FOR THE OZONIZATION OF α,β-UNSATURATED CYCLOHEXANONES TO 5-KETOALKANOIC ACIDS

[75] Inventor: Hubert J. Sharkey, Cincinnati, Ohio

[73] Assignee: National Distillers and Chemical Corporation, New York, N.Y.

[21] Appl. No.: 698,044

[22] Filed: Feb. 4, 1985

Related U.S. Application Data

[63] Continuation-in-part of Ser. No. 464,454, Feb. 7, 1983, abandoned.

[51] Int. Cl.$^4$ .............................................. C07C 51/34
[52] U.S. Cl. .................................... 562/577; 260/413
[58] Field of Search ......................... 562/577; 260/413

[56] References Cited

U.S. PATENT DOCUMENTS 4,414,418 11/1983 Lehky ................................. 562/577

OTHER PUBLICATIONS

Long, Chem. Reviews, vol. 27, 1940, pp. 437–493.

*Primary Examiner*—Werren B. Lone
*Attorney, Agent, or Firm*—Kenneth D. Tremain; Gerald A. Baracka

[57] ABSTRACT

An improved process for the ozonization of α,β-unsaturated cyclohexanones, most notably isophorone and piperatone, to produce 5-ketoalkanoic acids is provided. For the process, the α,β-unsaturated cyclohexanone is ozonized in an aliphatic monocarboxylic acid participating solvent which may optionally contain water and a soluble manganous salt.

12 Claims, No Drawings

PROCESS FOR THE OZONIZATION OF α,β-UNSATURATED CYCLOHEXANONES TO 5-KETOALKANOIC ACIDS

CROSS REFERENCE TO RELATED APPLICATION

This is a continuation-in-part of copending application Ser. No. 464,454 filed Feb. 7, 1983, now abandoned.

BACKGROUND OF THE INVENTION

FIELD OF THE INVENTION

The present invention relates to an improved process for the ozonization of α,β-unsaturated cyclohexanones whereby 5-ketoalkanoic acids are obtained in good yield.

DESCRIPTION OF THE PRIOR ART

Various oxidative procedures for the preparation of keto acids from dione cyclics are described in British patent application GB No. 2083035A published May 17, 1982. The British application is primarily concerned with methods for oxidatively cleaving isophorone to obtain 5-keto-3,3,-dimethylhexanoic acid which is the precursor of dimedone (1,1-dimethyl-3,5-diketocyclohexane)—a compound useful as a reagent for the detection of ethyl alcohol and the identification of aldehydes and for other industrial applications.

In addition to the conventional catalytic oxidation procedure described in the British application, wherein isophorone is oxidized using sodium periodate or sodium hypochlorite in the presence of ruthenium oxide catalyst, the use of ozone is also disclosed for the preparation of 5-keto-3,3-dimethylhexanoic acid. In one procedure ozone is reacted with isophorone in methanol and, upon completion of the ozonolysis, the resulting ozonized mixture decomposed by heating at 50°–60° C. for three hours with nitric acid. Heating ozonized mixtures at elevated temperatures in the presence of oxidizing agents and an organic solvent having a low flashpoint, is not, however, recommended for the large-scale preparation of 5-keto-3,3-dimethylhexanoic acid in view of the recognized thermal instability and reports of spontaneous decomposition of ozonized mixtures.

The ozonolysis of the α,β-unsaturated cyclic ketone is therefor carried out in a two-phase mixture of an aqueous phase and an organic solvent phase in the presence of an alkali metal hydroperoxide and a phase transfer catalyst. While this method makes it possible to conduct the reaction at much lower temperatures, the process still requires the use of a strong oxidizing agent (hydroperoxide) with the ozone and the use of expensive and highly toxic organic solvents (chloroform or methylene chloride). Furthermore, the bi-phase systems require the use of a phase transfer catalyst in order to accomplish the reaction.

It would be highly desirable if a process were available whereby α,β-unsaturated cyclic ketones, such as isophorone, could be efficiently and safely ozonized to the corresponding keto acids. It would be particularly advantageous if such a process did not require the use of strong mineral acids, peroxides or hydroperoxides for the ozonization or decomposition or the use of flammable or otherwise potentially hazardous organic solvents. The process would be even more desirable if the presence of a phase transfer catalyst was not required.

SUMMARY OF THE INVENTION

I have now quite unexpectedly discovered a process whereby all of the above advantages are realized. The process of this invention involves the ozonization of α,β-unsaturated cyclohexanones in the presence of a participating lower aliphatic monocarboxylic acid solvent to produce 5-ketoalkanoic acids in good yield with minimal undesirable oxidative by-products. The process does not require the use of strong mineral acid, peroxide or hydroperoxide oxidizing agents, flammable or highly toxic solvents or phase transfer catalysts.

For the invention, an α,β-unsaturated cyclohexanone of the formula

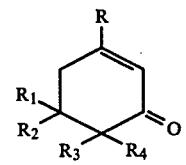

where R is a $C_{1-18}$ alkyl group and $R_1$, $R_2$, $R_3$ and $R_4$ are hydrogen or $C_{1-4}$ alkyl is contacted with ozone at a temperature from about 15° to 50° C. in an aliphatic monocarboxylic acid participating solvent to produce the corresponding 5-ketoalkanoic acid. Useful participating solvents include lower aliphatic monocarboxylic acids containing from 1 to 6 carbon atoms. Acetic acid and propionic acid are especially useful participating solvents for the process. There may also be present with the aliphatic monocarboxylic acid up to as much as 50 weight percent water. In a particularly useful embodiment of the invention, 0.001 to 1.0 weight percent, based on the α,β-unsaturated cyclohexanone, of a soluble manganous salt is also employed. Manganous carboxylates of lower carboxylic acids are particularly advantageous. The process is especially useful for the production of 5-keto-3,3-dimethylhexanoic acid from isophorone and 5-keto-2-isopropylhexanoic acid from piperatone.

DETAILED DESCRIPTION

This invention relates to a process for the ozonization of α,β-unsaturated cyclohexanones in the presence of a lower aliphatic monocarboxylic acid to obtain 5-ketoalkanoic acids. α,β-unsaturated cyclohexanones employed for the process have the general formula

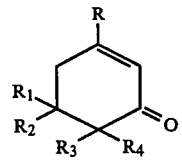

where R is an alkyl group having from 1 to about 18 and, more preferably, 1 to 4 carbon atoms and $R_1$, $R_2$, $R_3$ and $R_4$ are hydrogen or a $C_{1-4}$ alkyl group. Illustrative cyclohexanones include 3-methyl-2-cyclohexene-1-one; 3,5,5-trimethyl-2-cyclohexene-1-one (isophorone) and 3-methyl-6-isopropyl-2-cyclohexene-1-one (piperatone). In a particularly useful embodiment of the invention R is methyl and $R_1$, $R_2$, $R_3$ and $R_4$ are hydrogen or methyl.

The process is described by the general equation

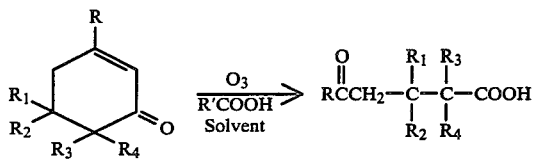

where R, $R_1$, $R_2$, $R_3$ and $R_4$ are the same as defined above. In the case where R is methyl, 5-ketohexanoic acids are produced. For example, when the $\alpha,\beta$-unsaturated cyclohexanone is isophorone or piperatone, 5-keto-3,3-dimethylhexanoic acid and 5-keto-2-isopropylhexanoic acid are respectively obtained.

For the reaction, the above-described $\alpha,\beta$-unsaturated cyclohexanones are contacted with ozone in a suitable saturated participating aliphatic monocarboxylic acid solvent. Useful aliphatic monocarboxylic acids have the formula R'COOH where R' is an alkyl radical having from 1 to 6 carbon atoms and the $C_{1-4}$ aliphatic monocarboxylic acids, i.e., formic acid, acetic acid, propionic acid and butyric acid, are preferred. Acetic acid and propionic acid are particularly advantageous participating solvents for use in the process of this invention. The $\alpha,\beta$-unsaturated cyclohexanone can constitute from about 10 to 50 percent by weight of the reaction mixture and, most generally, from about 20 to 40 percent by weight of the $\alpha,\beta$-unsaturated cyclohexanone is present in the participating solvent.

In one embodiment of the invention, the aliphatic monocarboxylic acid will also contain some water. The water can be present in an amount from 0.1 up to as much as 50 percent by weight of the participating solvent but most generally ranges from about 1 to 40 percent by weight of the aliphatic monocarboxylic acid. The amount of water will generally not exceed the solubility limits of the particular aliphatic monocarboxylic acid employed, however, it is possible to exceed the solubility limits and still successfully carry out the reaction. In some instances the initial reaction mixture may consist of two phases but as the ozonization proceeds a single phase will be obtained.

For the process, the $\alpha,\beta$-unsaturated cyclohexanone is contacted with ozone in the presence of the aliphatic monocarboxylic acid or acid mixture at a temperature in the range of 15° C. to 50° C. While it is possible to conduct the reaction at temperatures above 50° C., generally up to as high as 70° C., higher temperatures are generally avoided for safety reasons and to avoid inordinately high solvent losses. Also, the formation of undesirable by-products is minimized by operating within the 15°–50° C. temperature range. Temperatures below 15° C., down to the freezing point of the reaction mixture, can be employed but reaction rates are generally unacceptable. It is difficult to disperse the ozone in the higher viscosity solutions at these lower temperatures. The ozonization can be conducted as a batch, continuous, or semicontinuous operation at atmospheric, subatmospheric, or superatmospheric pressure. Pressure is not critical, however, it is most convenient to carry out the reaction at atmospheric or essentially atmospheric pressure.

It is preferable in carrying out the ozonization that the ozone be combined with a carrier gas such as argon, neon, nitrogen, oxygen, air, carbon dioxide or mixtures thereof. In this way it is possible to achieve more uniform reaction rates and more effectively meter and control the ozone concentration in the reactor. Excellent results are obtained when the carrier gas is oxygen or air or a mixture thereof and when the gas mixture contains from about 0.1 to about 15 percent by weight ozone and, more preferably, from about 1 to 5 percent by weight ozone.

Contact of the ozone and $\alpha,\beta$-unsaturated cyclohexanone and aliphatic monocarboxylic acid, with or without water, is accomplished using a suitable reactor or absorber. If the process is conducted as a batch operation, the $\alpha,\beta$-unsaturated cyclohexanone is combined with the participating solvent in the reactor and ozone introduced below the surface of the liquid and intimately dispersed through the liquid using a suitable gas dispersing means. Vigorous agitation may be necessary in some cases to obtain acceptable gas/liquid contact in the reactor.

To obtain the 5-ketoalkanoic acid requires that a stoichiometric amount of ozone be reacted with the $\alpha,\beta$-unsaturated cyclohexanone, i.e., 1 mol ozone is reacted per mol of olefin. In most cases, however, and particularly in batch type operations, an excess of ozone is employed to ensure that all of the $\alpha,\beta$-unsaturated cyclohexanone is reacted. The rate of ozone addition is governed by the uptake which will vary with the temperature of reaction, concentration of $\alpha,\beta$-unsaturated cyclohexanone in the reaction mixture, etc. The amount of ozone utilized upon passing through the reaction mixture can be determined using the starch iodide test. For this test, the effluent gas is scrubbed with aqueous potassium iodide and the free iodine formed thereby is titrated with sodium thiosulfate using a starch indicator.

Numerous modifications of the above-described procedures are possible, particularly when operating in a continuous mode, and will be apparent to those skilled in the art. It will be evident that the manner of charging the $\alpha,\beta$-unsaturated cyclohexanone, the participating aliphatic monocarboxylic acid solvent and the ozone or ozone-containing gases is not critical and various methods can be employed. Similarly, many variations for metering and determining the concentration of materials in the reactor, feed streams and effluent gases and for recycling effluent gases are possible.

An advantage of the present process is the fact that it is not necessary to treat the reaction mixture obtained upon ozonolysis with a strong oxidizing agent, such as mineral acid, peroxide, hydroperoxide, or the like, in order to achieve decomposition of the active oxygen species formed by reaction of the $\alpha,\beta$-unsaturated cyclohexanone and ozone. With the process of this invention, the active oxygen species are decomposed at temperatures within the range specified for the ozonization. In some cases, depending on the reaction conditions, decomposition of the active oxygen species is essentially complete when ozone addition is terminated. In other cases, however, it may be necessary to hold the reaction mixture at a temperature in the range 15° C. to 50° C. for a period of time until decomposition of the active oxygen species is complete, i.e., a negative starch iodide test is obtained. The amount of time necessary to completely decompose the active oxygen species is, of course, dependent on the temperature employed for the decomposition. It may require several days if ambient or lower temperatures are employed, whereas at 40° C. to 50° C., complete decomposition is obtained generally in less than two hours. In an especially useful embodiment of this invention, the ozonized reaction mixture is heated at 40° C. to 50° C. until a negative starch iodide test (indicating complete decomposition of active oxygen species) is obtained. In those instances where very rapid but controlled decomposition is desired, such as in a continuous operation, the reaction mixture obtained from the ozonization can be slowly introduced into a refluxing saturated aliphatic monocarboxylic acid having a boiling point in the range 100° C. to 120° C., most preferably, acetic acid. Water can also be utilized for this purpose. In none of the above decomposition procedures, however, are strong oxidizing agents, catalysts, or other adjuncts which tend to produce undesirable by-products required to accomplish the decomposition.

The resulting crude reaction product obtained after the active oxygen species has been dissipated and which consists primarily of 5-ketoalkanoic acid and participating solvent (with or without water) is worked up in the conventional manner. This typically involves first stripping the product at an elevated temperature under a moderate vacuum to remove the bulk of the participating solvent and any water which may be present. The stripped product is then further fractionated to recover the 5-ketoalkanoic acid. When isophorone is ozonized in a mixture of acetic acid and water, for example, the crude product obtained after the active oxygen species has been allowed to decompose is stripped up to a temperature of 140° C.–150° C. and pressure of 50 mm Hg. The resulting product is then fractionated and 5-keto-3,3-dimethylhexanoic acid (B.P. 96°–101° C. at 0.2 mm Hg) collected. Prior to heating to the temperatures necessary for stripping and distillation, it is essential that all active oxygen species be allowed to decompose, otherwise spontaneous (uncontrolled) decomposition can occur.

In a particularly useful embodiment of this invention, a small amount of manganese in the +2 oxidation state is included with the $\alpha,\beta$-unsaturated cyclohexanone and participating aliphatic monocarboxylic acid solvent. The presence of manganese appears to expedite the reaction and also serves as a useful indicator to control the rate of addition of ozone and determine at what point the addition of ozone can be terminated. When a substantial excess of ozone is present in the reaction mixture, the manganous ion is rapidly oxidized to the +3 oxidation state which results in a marked darkening in the color of the reaction mixture. Therefore, by visual observation, ozone consumption can be readily monitored and the rate of addition of ozone controlled for more effective utilization. When the ozone balance is restored, the reaction mixture will regain its original light color. As the reaction proceeds and when essentially all of the $\alpha,\beta$-unsaturated ketone has been reacted, the reaction mixture darkens due to the rapid increase in the ozone concentration. At this point ozone addition should be terminated. Any soluble salt of manganese in the +2 oxidation state can be employed, e.g., sulfate, carbonate, chloride, and generally will be used in an amount from about 0.001 to 1.0 weight percent, based on the $\alpha,\beta$-unsaturated cyclohexanone. Manganous carboxylates of $C_{1-4}$ carboxylic acids, and particularly manganous acetate, are especially advantageous for this purpose.

The following examples are provided to more fully illustrate the process of this invention. In these examples, all parts and percentages are on a weight basis unless otherwise indicated.

EXAMPLE I

To a one-hundred milliliter glass reaction cylinder were charged 16.6 grams isophorone and 20 grams glacial acetic acid. A mixture of ozone and oxygen (approximately 4% $O_3$) was then slowly introduced into the bottom of the cylinder through a glass frit and bubbled through the reaction mixture at ambient temperature and pressure. A small amount of foam was observed. Essentially complete uptake of the ozone was obtained at the beginning of the reaction, however, as the reaction continued an increasing amount of ozone was present in the effluent gas. Only about 30 percent of the ozone was utilized after approximately two hours and the reaction was terminated. The mixture was warmed to 50° C. and heating continued until a negative starch iodide test was obtained. The temperature was then increased up to about 140° C. and a vacuum of approximately 100 mm Hg applied to remove essentially all the acetic acid. The resulting crude product was vacuum distilled and 16.0 grams 5-keto-3,3-dimethylhexanoic acid collected over the boiling range 94° C.–114° C. (0.1 mm Hg).

EXAMPLE II

In a manner similar to that described in Example I, 30 grams isophorone in 57 grams aqueous acetic acid (35% $H_2O$) was ozonized at ambient temperature and pressure in a 300 ml glass cylinder for approximately 5 ½ hours. The resulting reaction product was then slowly dropped into a small amount of refluxing acetic acid, stripped at 140° C. under vacuum to remove water and acetic acid, and then vacuum distilled. Ninety-five percent yield of high purity 5-keto-3,3-dimethylhexanoic acid was obtained boiling in the range 96° C.–106° C. (0.1 mm Hg).

EXAMPLE III

In accordance with the usual procedure 41 grams isophorone in 45 grams aqueous acetic acid (50% $H_2O$) was ozonized at ambient temperature and pressure for approximately two hours. Additional acetic acid (60 mls) and water (30 mls) were added and treatment with ozone continued. After 8 hours no further ozone uptake was observed and the reaction was terminated. The resulting reaction product was then slowly added to refluxing acetic acid over a period of about one hour and, when a negative test was obtained using starch iodide, the water and acetic acid were stripped by gradually heating to 150° C. under a vacuum of 50–100 mm Hg. Distillation of the resulting crude product yielded 40.3 grams 5-keto-3,3-dimethylhexanoic acid (B.P. 96° C.–101° C. at 0.2 mm Hg) which was indicated by gas-liquid chromatography to be 99 percent pure.

EXAMPLE IV

In accordance with the general procedure, 30 grams of piperatone was charged to a reactor with 95 grams aqueous acetic acid (31% $H_2O$) and contacted with ozone at a temperature of 50° C.–70° C. After four hours, ozone absorption was only 5 percent and the ozone addition was discontinued. The reaction product was slowly added to refluxing acetic acid and when a negative starch iodide test was obtained, stripped in the usual manner to remove acetic acid and water. The resulting crude 5-keto-2-isopropylhexanoic acid was vacuum distilled at 0.1 mm Hg and the fraction boiling at 115° C.–130° C. retained. Analysis by gas chromatography indicated the product to be approximately 98.8% pure 5-keto-2-isopropylhexanoic acid. An 80 percent yield was obtained for this reaction.

EXAMPLE V

To demonstrate the versatility of the present process and the advantage of utilizing a small amount of manganese with the α,β-unsaturated cyclohexanone and participating solvent, 28 grams isophorone in 95 grams aqueous acetic acid (31% $H_2O$) was ozonized in the usual manner except that 0.2 grams manganous acetate [$Mn(OAc)_2 \cdot 4H_2O$] was added. The ozonization was carried out at ambient temperature and pressure and after about 4 hours a noticeable darkening of the reaction mixture was observed. Analysis of the effluent gas indicated 50 percent ozone absorption. Ozone addition was continued at the same rate for an additional 30 minutes during which time the reaction mixture became very dark. Addition of ozone was discontinued at this point and the reaction mixture allowed to stand for approximately 12 hours after which time the original light-yellow color of the mixture was restored. Ozone addition was restarted and continued for 3 hours after which time the dark color reappeared and a negative starch iodide test was obtained. The reaction mixture was then heated to 140° C. under vacuum (50 mm Hg) to remove acetic acid and water. Vacuum distillation of the resulting crude product at 0.1 mm Hg provided 85 percent yield 5-keto-3,3-dimethylhexanoic acid of high purity.

EXAMPLE VI

Isophorone was ozonized in the presence of 0.23% manganous acetate. For the reaction 43 grams isophorone, 120 grams acetic acid, 60 grams water and 100 milligrams $Mn(OAc)_2 \cdot 4H_2O$ were charged to the reactor and ozonized in the usual manner at ambient temperature and pressure. The essentially colorless reaction mixture developed a slight greenish coloration after about three hours and after six hours was dark brown. Ozone addition was terminated at this point. The absence of active oxygen made any decomposition precautionary step unnecessary and the reaction mixture was directly treated under vacuum to strip off acetic acid and water. Vacuum distillation of the resulting crude product at 0.3 mm Hg gave an 87 percent yield of 96.5% pure 5-keto-3,3-dimethylhexanoic acid boiling in the range 95° C. to 100° C.

EXAMPLE VII

In a manner similar to that described in Example VI, 42 grams isophorone in 60 grams acetic acid and 60 grams water and containing 450 milligrams $Mn(OAc)_2 \cdot 4H_2O$ was ozonized for 8 hours at ambient temperature and pressure. The dark brown reaction mixture was allowed to stand overnight where upon a negative starch iodide test was obtained and the mixture was stripped to remove water and acetic acid and then vacuum distilled at 0.1-0.3 mm Hg. Eighty-five percent yield of 95% pure 5-keto-3,3-dimethylhexanoic acid (boiling range 105° C.-110° C. at 0.1 to 0.3 mm Hg) was obtained upon further distillation.

EXAMPLE VIII

To demonstrate the ability to carry out the ozonization using a mixture of ozone and air the following experiment was conducted. For the reaction, 45.55 grams piperatone, 170 grams aqueous acetic acid (32% $H_2O$) and 100 milligrams $Mn(OAc)_2 \cdot 4H_2O$ were charged to a reactor and heated to about 30° C. An ozone/air mixture (1-2% $O_3$) was subsequently introduced into the solution through a glass frit over a period of about 11 hours. During the last few hours of the reaction there was a noticeable darkening of the reaction mixture. The active oxygen-free reaction mixture was then poured into 500 mls water and extracted several times with methylene chloride. Evaporation of the methylene chloride yielded 48.7 grams of a product which contained 91.5% 5-keto-2-isopropylhexanoic acid by chromatographic analysis. This represents an 86% yield, based on theory. If desired, this product can be vacuum distilled.

EXAMPLE IX

A reaction similar to that of Example VIII was carried out except that the manganous acetate was omitted. For this reaction 45 grams piperatone, 100 grams glacial acetic acid and 50 grams water were employed. The reaction mixture was ozonized, using a mixture of ozone and air, for 9 hours. The reaction mixture remained completely colorless throughout the ozonization. After termination of ozone addition, the reaction mixture was allowed to stand for about 14 hours and then dropped into a heel of refluxing acetic acid to decompose any remaining active oxygen species. When a negative starch iodide test was obtained the mixture was stripped under vacuum to reduce the volume and extracted with methylene chloride. Evaporation of the methylene chloride yielded 39.5 grams of a product which contained 84.2% 5-keto-2-isopropylhexanoic acid. This represents a 64% yield, based on theory.

EXAMPLE X

To demonstrate the ability to vary the aliphatic monocarboxylic acid participating solvent, 30 grams piperatone and 70 grams of 88 percent formic acid were charged to a reactor and a mixture of ozone and oxygen introduced subsurfacely at a rate of approximately 75 milliequivalents ozone per hour. The initial two-phase mixture had an intense red-purple color, however, as the ozone was introduced, the color was rapidly bleached to a light yellow and the reaction mixture became homogenous. Considerable foaming was observed. Treatment with ozone was continued for approximately 5 hours after which time the reaction mixture was stripped at 70° C. under aspirator vacuum to remove water and formic acid and decompose any active oxygen. Vacuum distillation of the resulting crude product gave 27.1 grams (79.4% yield) 5-keto-2-isopropylhexanoic acid (boiling range 114° C.-124° C. at 0.2 mm Hg). Gas/liquid chromatographic analysis indicated the 5-keto-2-isopropylhexanoic acid to be 95 percent pure.

EXAMPLE XI

In accordance with the procedure of this invention, piperatone was ozonized in propionic acid to obtain 5-keto-2-isopropylhexanoic acid. For the reaction, 61 grams piperatone, 61 grams propionic acid and 7 grams water were charged and treated with ozone in the usual manner. After about 8 hours, only 30% ozone absorption was obtained and the ozone addition was discontinued. The reaction mixture was heated at 60° C.-70° C. until a negative starch iodide test was obtained. Propionic acid and water were then removed by heating up to about 65° C. at 35 mm Hg. The crude product (97 grams) was steam distilled and dried under vacuum to obtain 66.6 grams (95.8% yield) of 96.2 percent pure 5-keto-2-isopropylhexanoic acid.

I claim:

1. A process for the preparation of 5-ketoalkanoic acids from α,β-unsaturated cyclohexanones which comprises:

(1) introducing ozone into a mixture of (a) an α,β-unsaturated cyclohexanone of the formula

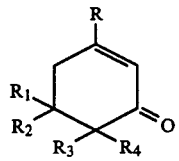

where R is a $C_{1-18}$ alkyl group and $R_1$, $R_2$, $R_3$, and $R_4$ are hydrogen or a $C_{1-4}$ alkyl group, (b) a $C_{1-6}$ saturated aliphatic monocarboxylic acid containing from 0.1 up to 50 percent by weight water, and (c) 0.001 to 1.0 weight percent, based on the α,β-unsaturated cyclohexanone, of a soluble manganous salt, said mixture maintained at a temperature from 15° C. to 50° C. and intimately contacted with said ozone until one mol ozone is reacted per mol of α,β-unsaturated cyclohexanone;

(2) terminating the addition of ozone and maintaining the temperature of the mixture in the range 15° C. to 50° C. until a negative starch iodide test is obtained; and (3) recovering the 5-ketoalkanoic acid.

2. The process of claim 1 wherein the α,β-unsaturated cyclohexanone constitutes from 10 to 50 percent by weight of the reaction mixture.

3. The process of claim 2 wherein R is methyl, the aliphatic monocarboxylic acid (b) contains from 1 to 4 carbon atoms and the soluble manganous salt (c) is a carboxylate of manganese derived from a $C_{1-4}$ saturated aliphatic monocarboxylic acid.

4. The process of claim 3 wherein the aliphatic monocarboxylic acid (b) is acetic acid or propionic acid containing from 1 to 40 percent by weight water and the α,β-unsaturated cyclohexanone is isophorone or piperatone.

5. The process of claim 4 wherein the α,β-unsaturated cyclohexanone constitutes from 20 to 40 percent by weight of the reaction mixture.

6. The process of claim 5 wherein the manganous carboxylate (c) is manganous acetate.

7. A process for the preparation of 5-ketoalkanoic acids from α,β-unsaturated cyclohexanones which comprises:

(1) introducing ozone into a mixture of (a) an α,β-unsaturated cyclohexanone of the formula

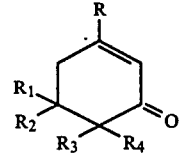

where R is a $C_{1-18}$ alkyl group and $R_1$, $R_2$, $R_3$, and $R_4$ are hydrogen or a $C_{1-4}$ alkyl group, (b) a $C_{1-6}$ saturated aliphatic monocarboxylic acid containing from 0.1 up to 50 percent by weight water, and (c) 0.001 to 1.0 weight percent, based on the α,β-unsaturated cyclohexanone, of a soluble manganous salt, said mixture maintained at a temperature from 15° C. to 50° C. and intimately contacted with said ozone until one mol ozone is reacted per mol of α,β-unsaturated cyclohexanone;

(2) terminating the addition of ozone and slowly introducing the mixture into a refluxing saturated aliphatic monocarboxylic acid having a boiling point in the range 100° C. to 120° C.; and (3) recovering the 5-ketoalkanoic acid.

8. The process of claim 7 wherein R is methyl, the aliphatic monocarboxylic acid (b) contains from 1 to 4 carbon atoms and the α,β-unsaturated cyclohexanone constitutes from 10 to 50 percent by weight of the reaction mixture.

9. The process of claim 8 wherein the soluble manganous salt (c) is a carboxylate of manganese derived from a $C_{1-4}$ saturated aliphatic monocarboxylic acid.

10. The process of claim 9 wherein the aliphatic monocarboxylic acid (b) is acetic acid or propionic acid containing from 1 to 40 percent by weight water and the α,β-unsaturated cyclohexanone is isophorone or piperatone.

11. The process of claim 10 wherein the α,β-unsaturated cyclohexanone constitutes from 20 to 40 percent by weight of the reaction mixture.

12. The process of claim 11 wherein the manganous carboxylate (c) is manganous acetate and in step (2) the aliphatic monocarboxylic acid is acetic acid.

* * * * *